(12) United States Patent
Gerlach et al.

(10) Patent No.: US 10,471,198 B2
(45) Date of Patent: Nov. 12, 2019

(54) BLOOD TREATMENT DEVICE COMPRISING A FUNCTIONAL UNIT FOR CARRYING OUT THE BLOOD TREATMENT AND METHOD FOR MONITORING THE FUNCTIONALITY AND/OR THE OPERATING STATE OF THE FUNCTIONAL UNIT

(71) Applicant: FRESENIUS MEDICAL CARE DEUTSCHLAND GMBH, Bad Homburg (DE)

(72) Inventors: Daniel Gerlach, Frankfurt (DE); Jurgen Hacker, Neu-Anspach (DE); Joachim Noack, Bad Neustadt (DE); Peter Scheunert, Friedrichsdorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 32 days.

(21) Appl. No.: 15/501,861

(22) PCT Filed: Jul. 21, 2015

(86) PCT No.: PCT/EP2015/066687
§ 371 (c)(1),
(2) Date: Feb. 6, 2017

(87) PCT Pub. No.: WO2016/020191
PCT Pub. Date: Feb. 11, 2016

(65) Prior Publication Data
US 2017/0232174 A1 Aug. 17, 2017

(30) Foreign Application Priority Data
Aug. 7, 2014 (DE) .................. 10 2014 011 695

(51) Int. Cl.
*A61M 1/16* (2006.01)
*G01M 3/38* (2006.01)
(Continued)

(52) U.S. Cl.
CPC ............ *A61M 1/1692* (2013.01); *G01M 3/38* (2013.01); *G08B 21/02* (2013.01); *A61M 1/3627* (2013.01);
(Continued)

(58) Field of Classification Search
CPC .......... A61M 1/1692; A61M 2205/331; A61M 2205/18; A61M 2205/50;
(Continued)

(56) References Cited

U.S. PATENT DOCUMENTS

| 4,166,961 A | * | 9/1979 | Dam | A61M 1/1692 |
| | | | | 250/573 |
| 4,818,190 A | * | 4/1989 | Pelmulder | A61M 5/365 |
| | | | | 417/360 |

(Continued)

FOREIGN PATENT DOCUMENTS

| EP | 0319279 | 6/1989 |
| EP | 0319279 A1 | 6/1989 |

(Continued)

OTHER PUBLICATIONS

International Preliminary Report on Patentability for corresponding International Patent Application No. PCT/EP2015/066687, dated Feb. 7, 2017, with corresponding Form PCT/IB/338 and Written Opinion of the International Searching Authority (Form PCT/ISA/237) (7 pages total).

(Continued)

Primary Examiner — Michael P LaPage
(74) *Attorney, Agent, or Firm* — Kilyk & Bowersox, P.L.L.C.

(57) ABSTRACT

The invention relates to a blood treatment device comprising an attachment unit 7 for attaching a functional unit 1 intended for single use for carrying out the blood treatment. The blood treatment device according to the invention is characterised by a monitoring unit 8 for monitoring the operability and/or the operating state of the functional unit 1, which functional unit comprises at least one light transmitter 17A, 18A and at least one light receiver 17B, 18B. The light transmitter and light receiver are arranged in the monitoring unit 8 according to the invention on one side of the functional unit 1. The arrangement of the light transmitter and light receiver on the same side has the advantage that the monitoring unit 8 can be integrated into the attachment unit 7 of the blood treatment device without any major structural modifications. The monitoring of the functional unit 1 is based on an optical measurement method in which the light reflected on a part of the functional unit 1 or a part of the attachment unit 7 is detected. A calculation- and evaluation unit 13 is configured such that conclusions can be drawn as to a defective state and/or a certain operating state of the functional unit 1 based on the intensity of the light falling on the functional unit and the light reflected on the functional unit or the attachment unit.

16 Claims, 2 Drawing Sheets

Figure 1:
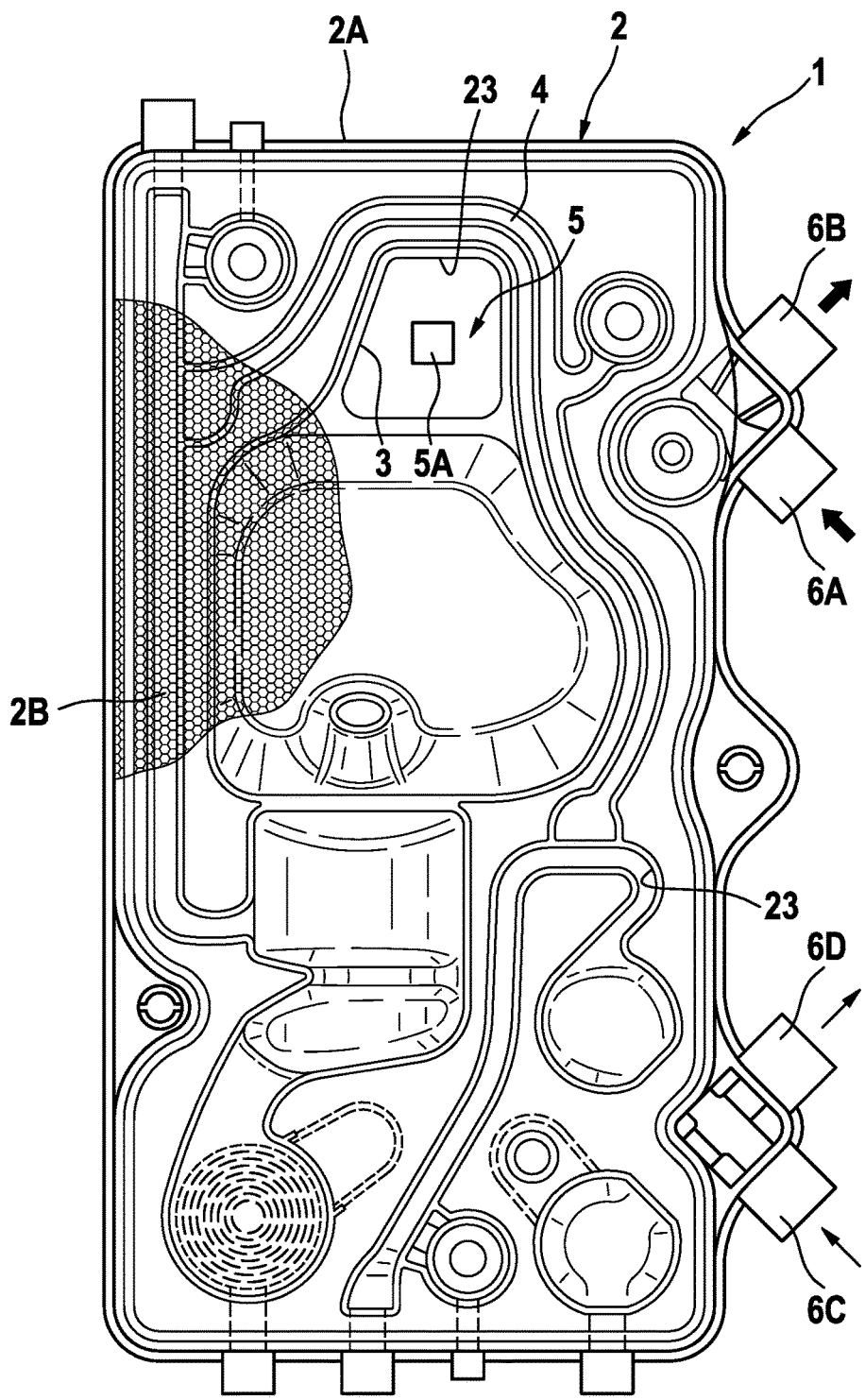

(51) Int. Cl.
*G08B 21/02* (2006.01)
*A61M 1/36* (2006.01)
*G01N 15/08* (2006.01)

(52) U.S. Cl.
CPC . *A61M 2205/121* (2013.01); *A61M 2205/122* (2013.01); *A61M 2205/14* (2013.01); *A61M 2205/15* (2013.01); *A61M 2205/18* (2013.01); *A61M 2205/3306* (2013.01); *A61M 2205/50* (2013.01); *A61M 2205/705* (2013.01); *A61M 2209/084* (2013.01); *G01N 2015/084* (2013.01); *G01N 2015/0846* (2013.01)

(58) Field of Classification Search
CPC .... A61M 2205/7536; A61M 2209/084; A61M 2205/15; A61M 2205/705; A61M 2205/3306; A61M 2205/14; A61M 2205/122; A61M 2205/121; A61M 1/3627; G01M 3/38; G08B 21/02; G01N 15/08; G01N 2015/0846; G01N 2015/084
See application file for complete search history.

(56) References Cited

U.S. PATENT DOCUMENTS

| | | | | |
|---|---|---|---|---|
| 5,601,080 | A | * | 2/1997 | Oppenheimer ...... G01N 21/532 356/39 |
| 6,510,330 | B1 | * | 1/2003 | Enejder ................ G01N 21/532 356/39 |
| 2009/0101552 | A1 | * | 4/2009 | Fulkerson ........... A61M 1/1692 210/103 |
| 2009/0279071 | A1 | * | 11/2009 | Bado .................. A61B 5/14557 356/40 |
| 2010/0206784 | A1 | * | 8/2010 | Weaver ............... A61M 1/3639 210/85 |
| 2010/0274168 | A1 | * | 10/2010 | Gronau ................... A61M 1/30 604/5.04 |
| 2011/0239742 | A1 | | 10/2011 | Müller |
| 2012/0030921 | A1 | | 2/2012 | Haecker |
| 2014/0132945 | A1 | | 5/2014 | Sandford |

FOREIGN PATENT DOCUMENTS

| | | |
|---|---|---|
| EP | 2221075 A1 | 8/2010 |
| WO | 2008100989 A2 | 8/2008 |
| WO | 2010066441 A1 | 6/2010 |
| WO | 2010102790 A2 | 9/2010 |
| WO | 2012161744 A2 | 11/2012 |
| WO | 2012161744 A9 | 11/2012 |

OTHER PUBLICATIONS

International Search Report and Written Opinion issued in corresponding International Patent Application No. PCT/EP2015/066687 (with English translation of International Search Report) dated Oct. 22, 2015 (13 pages).

* cited by examiner

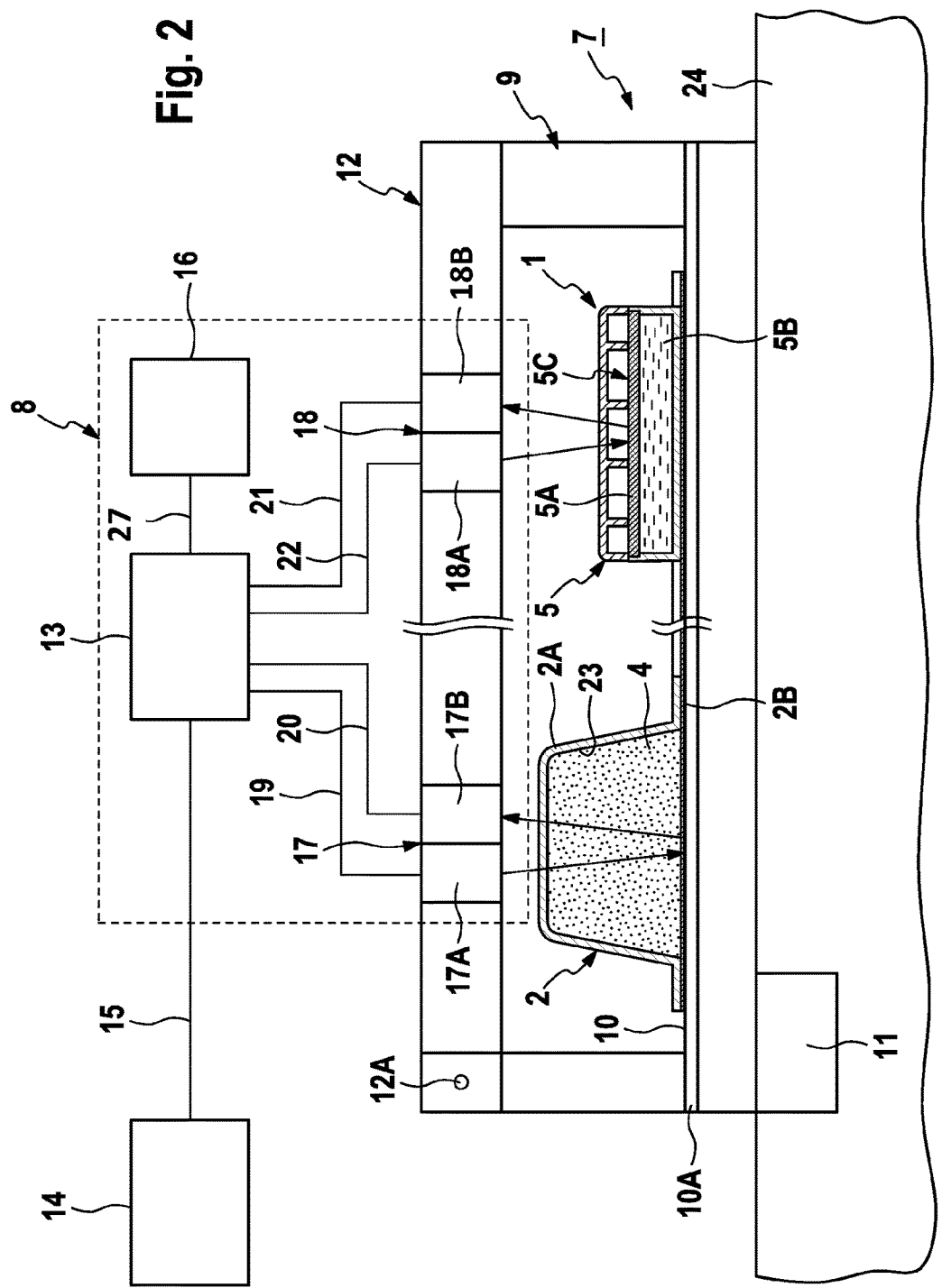

BLOOD TREATMENT DEVICE COMPRISING A FUNCTIONAL UNIT FOR CARRYING OUT THE BLOOD TREATMENT AND METHOD FOR MONITORING THE FUNCTIONALITY AND/OR THE OPERATING STATE OF THE FUNCTIONAL UNIT

This application is a National Stage Application of PCT/EP2015/066687, filed Jul. 21, 2015, which claims priority to German Patent Application No. 10 2014 011 695.6, filed Aug. 7, 2014, which are incorporated in their entireties by reference herein.

The invention relates to a blood treatment device comprising an attachment unit for attaching a functional unit intended for single use for carrying out the blood treatment and a monitoring unit for monitoring the operability and/or the operating state of the functional unit. Furthermore, the invention relates to a method for monitoring the operability and/or the operating state of a functional unit which is attached to an attachment unit of a blood treatment device for carrying out a blood treatment.

The known blood treatment devices comprise an extracorporeal blood circuit and a dialysate system. Blood treatment devices are known in which parts of the extracorporeal blood circuit and of the dialysate system form constituent parts of a functional unit intended for single use (disposable). Such blood treatment devices comprise an attachment unit to which the functional unit is attached for carrying out the blood treatment.

DE 10 2009 018 664 A1 describes an external functional unit for an extracorporeal blood treatment device. The functional unit has a transparent housing body in which channels and chambers for blood and dialysate are formed. Blood and dialysate are supplied by means of hose lines which are connected to inlets and outlets of the housing body. The known functional units are also known as cassettes.

An attachment unit for attaching an external functional unit is known from DE 10 2009 012 633 A1. The attachment unit has a fixed attachment component and a pivotable attachment component, the functional unit being held in a clamped manner between the fixed attachment component and the pivotable attachment component.

WO 2010/066441 A1 describes an attachment unit for a functional unit of an extracorporeal blood treatment device with which the functional unit is held by the creation of a vacuum at a contact surface of the attachment unit.

When carrying out an extracorporeal blood treatment, there is, in principle, the risk that the patient's blood will find its way from the extracorporeal blood circuit into the dialysate system. This is possible in the event of a rupture of the semipermeable membrane of the dialyser. Thus, with the known blood treatment devices the entry of blood into the dialysate system is monitored. In the prior art, blood (haemoglobin) in the dialysate system is detected by means of a photometric measurement method in which the reduction in the intensity of a ray passing through the dialysate as a result of the entry of blood is detected. A spectroscopic blood leak detector is known from DE 10 2006 029 899 B4, for example.

The use of an external functional unit for carrying out a blood treatment entails the risk of blood entering the dialysate or the substitution fluid if leakages occur at the joins of the housing body. For example, leaks may occur between adjacent chambers and channels of the housing body.

The object of the invention is to improve the safety of the blood treatment when an external functional unit is used for carrying out the blood treatment. In particular, the object of the invention is to provide a blood treatment device comprising an easy-to-use attachment unit for attaching a functional unit for carrying out the blood treatment, which allows the monitoring of the operability and/or the operating state of the functional unit with a high degree of reliability.

These objects are achieved according to the invention by means of the features of the independent claims. The subject matter of the dependent claims relates to advantageous embodiments of the invention.

The blood treatment device according to the invention is characterised by a monitoring unit (disposable) for monitoring the operability and/or the operating state of the functional unit, which comprises at least one light transmitter and at least one light receiver. The light transmitter and light receiver may be components of an apparatus for transmitting and receiving light. This apparatus may, for example, be configured as an LED array.

In the monitoring unit according to the invention, the light transmitter and light receiver are arranged on one side of the functional unit. The arrangement of the light transmitter and light receiver on the same side has the advantage that the monitoring unit can be integrated into the attachment unit of the blood treatment device without any major structural modifications.

The monitoring of the functional unit is based on an optical measurement method in which the light reflected on a part of the functional unit or a part of the attachment unit is detected. The calculation- and evaluation unit is configured such that conclusions can be drawn as to a defective state and/or a certain operating state of the functional unit based on the intensity of the light falling on the functional unit and of the light reflected on the functional unit or attachment unit.

If, for example, blood from the blood side enters the dialysate side owing to a defective functional unit, the defective state can be detected with the functional unit. For instance, it can be detected whether blood from a blood chamber or a blood-carrying channel has entered a dialysate chamber or a channel carrying dialysate or substitution fluid owing to a leak in the housing body of the functional unit. The entry of blood can easily be detected in accordance with the known method of detecting haemoglobin. Moreover, it can be detected whether a certain fluid, in particular blood, dialysate or substitution fluid, is present in a channel or a chamber of the functional unit or whether the chambers or channels of the functional unit are filled with any fluid at all. The blood treatment device according to the invention therefore allows not only the monitoring of the operability but also of the operating state of the functional unit.

In a preferred embodiment, which is characterised by being easy to use, the attachment unit comprises an attachment component and a cover component which are arranged so as to be at such a distance from one another that the functional unit can be placed between the attachment component and the cover component. In this embodiment the light transmitter and the light receiver are preferably provided on the cover component. It is, however, also possible for the light transmitter and the light receiver to be provided on the attachment component.

In a further particularly preferred embodiment in which the light transmitter and light receiver are provided on the cover component, the attachment component of the attachment unit comprises a contact surface for the functional unit, which reflects the light of the light transmitter. The light falling on the functional unit and passing through the functional unit is reflected on the contact surface of the attachment component for the optical reflection measurement, so that the light can be transmitted and received on the same side of the functional unit.

The cover component of the attachment unit is preferably attached to the attachment component so as to be movable between an open and a closed position, so that the functional unit can easily be inserted into the attachment unit. The cover component is preferably formed as a door which seals off the receiving space of the attachment component for receiving the functional unit.

The cover component of the attachment unit may be formed as a clamp component so that the functional unit can be attached in a clamped manner between the attachment component and the cover component.

An alternative embodiment provides for the attachment unit having a suction unit for creating a vacuum at the attachment component so that the functional unit can be attached to the attachment component by way of suction power. In this embodiment, the contact surface of the attachment component preferably comprises a flexible material which the functional unit abuts. The flexible material preferably forms a reflective contact surface on which the light is reflected.

In the preferred embodiments, the advantages of the arrangement of the light transmitter and light receiver in or on the cover component lie particularly in the fact that the attachment component can be formed having a contact surface that is not penetrated by components of the light transmitter and light receiver. In particular, in the embodiment having the contact surface comprising a flexible material, no openings are required in the flexible material for the light to pass through, which would be disadvantageous in terms of a simple purification of the flexible material.

Furthermore, the advantages of the invention can particularly be seen in a functional unit in which a chamber or a channel has an opening which is sealed off with a hydrophobic membrane, i.e. a functional unit in which one or more hydrophobic filters are integrated. In a functional unit of this type, the monitoring unit allows not only the monitoring of the channels carrying blood and/or dialysate but also of the hydrophobic filter through which blood may escape in the event of a rupture. For the monitoring of the hydrophobic filter, it is not the light reflected on the attachment unit but rather the light reflected on a part of the functional unit, i.e. the light reflected on the hydrophobic membrane, that is detected. In the event of a malfunction, blood penetrates into the fibres on the reverse side of the membrane and stains the membrane red, so that the intensity of the reflected light changes, which is detected by the monitoring unit.

The light transmitter and light receiver of the monitoring unit can also detect whether the functional unit is attached to the attachment unit since the housing body of the functional unit absorbs light.

Different criteria can be established for the different cases, such that conclusions can be drawn as to the operability and/or the operating state of the functional unit as a function of the reduction of the reflected light.

In the following, an embodiment of the invention will be described in detail by reference to the drawings.

FIG. 1 shows a functional unit for carrying out the blood treatment for a blood treatment device in plan view, and FIG. 2 shows the attachment unit together with the functional unit of the blood treatment device as an extremely simplified schematic representation.

FIG. 1 shows an embodiment of an external functional unit (disposable) for an extracorporeal blood treatment device, in particular a haemodialysis device. The functional unit 1 comprises a flat housing body 2 which consists of a material permeable to light. The housing body 2 may be a transparent plastics body. The functional unit is described in detail in DE 10 2009 018 664 A1, to which reference is explicitly made. The components of the functional unit that are essential to the invention are described below.

FIG. 1 shows the functional unit 1 in a view from below. The housing body 2 of the functional unit 1 comprises a housing part 2A formed having trough-shaped recesses 23, which housing part is tightly sealed off at the underside with a film 2B (shown only in part) by the formation of a plurality of chambers and channels. During operation of the haemodialysis device, blood or a medicinal fluid, for example dialysate or substitution fluid, is present in the chambers and channels.

In FIG. 1, one of the chambers is denoted by reference sign 3 and one of the channels is denoted by reference sign 4. Blood is present in the chamber 3 during operation of the dialysis device. The channel 4 is a channel in which substitution fluid flows during operation of the dialysis device. Moreover, the functional unit 1 comprises a hydrophobic filter 5 which has a hydrophobic membrane 5A (merely indicated in FIG. 1). Furthermore, the functional unit 1 also has a valve arrangement (not shown in more detail in FIG. 1) having a plurality of valves via which the fluid connections between the individual chambers and channels can be established.

The blood and the medical fluids are supplied and led away by means of hose lines (not shown) which are connected to connectors 6A to 6D of the housing body 2. The hose lines (not shown) are, together with further components (which are not shown) where appropriate, a part of the functional unit 1.

FIG. 2 shows as an extremely simplified schematic representation the part of the housing 24 of the blood treatment device where an attachment unit 7 for attaching the functional unit 1 is located. FIG. 2 only shows the components of the functional unit 1 and the attachment unit 7 that are essential to the invention. A monitoring unit 8 for monitoring the operability and/or the operating state of the functional unit is also shown in FIG. 2.

The functional unit 1 is inserted into the attachment unit 7. FIG. 2 shows a cross-section of the functional unit 1. In the sectional view, the substitution fluid channel 4 and the hydrophobic filter 5 comprising the hydrophobic membrane 5A can be seen. The rest of the chambers and channels are not shown for the sake of clarity.

The hydrophobic filter 5 comprises a chamber 5B in the housing body 2, which has an opening 5C on the upper surface. The opening 5C of the chamber 5B is tightly sealed by the hydrophobic membrane 5A. Above the hydrophobic membrane 5C, the housing body 2 is formed as a support structure so that the hydrophobic membrane is fixed in the housing body. During operation of the haemodialysis device, for example in single-needle mode, the chamber 5B of the hydrophobic filter 5 is filled with blood.

The attachment unit 7 of the blood treatment device comprises an attachment component 9 on the machine side, which is formed as a housing open on one side for receiving the functional unit 1.

For carrying out the blood treatment, the functional unit 1 is inserted into the attachment component 9, the lower surface of the functional unit 1 abutting a contact surface 10 of the attachment component 9. The attachment unit 7 comprises a suction unit 11 which creates a vacuum at the contact surface 10 so that the functional unit 1 is sucked in at the contact surface 10.

Moreover, the attachment unit 7 comprises a cover component 12 which is attached to the attachment component 9 such that it can pivot about an axis 12A. The cover component 12 is opened for inserting the functional unit and closed for the operation of the blood treatment device.

The monitoring unit 8 for monitoring the operability and/or the operating state of the functional unit 1 will be described in the following.

The monitoring unit 8 comprises a calculation- and evaluation unit 13 which may also be a component of the central control unit 14 of the blood treatment device. The calculation- and evaluation unit 13 is connected to the central control unit 14 via a data line 15, so that calculation- and evaluation unit 13 can receive signals which signalise the operating state of the blood treatment device. An alarm unit 16 is connected to the calculation- and evaluation unit 13 via a data line 27. Furthermore, the monitoring unit 8 comprises a first transmitting- and receiving unit 17 and a second transmitting- and receiving unit 18 which transmit and receive light.

The first and second transmitting- and receiving units 17, 18 each comprise a light transmitter 17A, 18A and a light receiver 17B, 18B. The light transmitter and the light receiver may be light-emitting diodes (LEDs). The light-emitting diodes of the light transmitter preferably transmit light having a wavelength corresponding to the absorption peak of haemoglobin. The effect of this is that the monitoring unit 8 has maximum sensitivity for detecting blood.

Light transmitter and light receiver 17A, 17B of the first transmitting- and receiving unit 17 is arranged on the cover component 12 of the attachment unit 7 above the substitution fluid channel 4, while the light transmitter and light receiver 18A, 18B of the second transmitting- and receiving unit 18 is arranged above the hydrophobic membrane 5A of the hydrophobic filter 5 in the cover component 12.

The light transmitter 17A and light receiver 17B of the first transmitting- and receiving unit 17 are arranged such that all of the light of the light transmitter 17A is reflected on the contact surface 10 of the attachment component 9 and hits the light receiver 17B. In a preferred embodiment, the contact surface 10 of the attachment component 9 is covered with a flexible material, for example a plastics mat 10A, which the functional unit 1 abuts. The plastics mat 10A is designed such that the light rays are reflected. For instance, the flexible material may be provided with a reflective coating.

The light transmitter 18A and light receiver 18B of the second transmitting- and receiving unit 18 are arranged above the hydrophobic filter 5 in such a manner that the rays from the light transmitter 18A are reflected by the hydrophobic membrane 5A and hit the light receiver 18B.

The calculation- and evaluation unit 13 receives the signals of the light transmitter and light receiver 17A, 17B; 18A, 18B via data lines 19, 20, 21, 22. The calculation- and evaluation unit 13 is configured such that conclusions can be drawn as to a defective operating state and/or a certain operating state of the functional unit based on a reduction of the intensity of the reflected light; in particular it can be concluded that there has been a leakage of blood. The calculation- and evaluation unit 13 may detect a leakage of blood for example on the basis of a measurement based on Lambert's law. Such optical measurement methods can be found in the prior art.

If, when the functional unit 1 is defective, blood ends up in the substitution fluid, the light of the light transmitter 17A is absorbed by the haemoglobin in the substitution fluid so that the intensity of the light is reduced. If the calculation- and evaluation unit 13 has detected such a malfunction, the calculation- and evaluation unit 13 generates an alarm signal which is received by the alarm unit 16 via the data line 27. Furthermore, the calculation- and evaluation unit 13 generates a control signal which is received by the central control unit 14 of the blood treatment device via the data line 15, so that the control unit 15 can make an intervention in the machine control.

If the hydrophobic membrane 5A of the hydrophobic filter 5 is defective, blood seeps into the membrane so that the membrane is stained red. Thus, the intensity of the reflected light received by the light receiver 18B changes, and therefore the calculation- and evaluation unit 13 once again generates an alarm signal and a control signal for the alarm unit 16 and the control unit 14. The monitoring unit 8 therefore allows the monitoring of all regions of the functional unit where leakages can occur. For this purpose, the monitoring unit may also comprise further transmitting- and receiving units.

In addition to operability, the monitoring unit 8 also monitors the operating state of the functional unit. If the functional unit 1 comprising the transparent housing body 2 is inserted into the attachment unit 7, the intensity of the reflected light changes. On the basis of the signal level of the light receiver 17B for example of the first transmitting- and receiving unit 17, the calculation- and evaluation unit 13 detects whether the functional unit is inserted by comparing the measured signal level with a predetermined reference level. This reference level can be set by means of calibration measurements and stored in a memory of the calculation- and evaluation unit 13.

Furthermore, the calculation- and evaluation unit 13 can detect whether the substitution fluid channel 4 is filled with substitution fluid. The filling of the substitution fluid channel with substitution fluid once again results in the light being absorbed. For the measurement, a further reference level can be set which is stored in the memory of the calculation- and evaluation unit 13. It is also possible to detect the fill level when corresponding reference levels are set.

The monitoring unit 8 can be tested and/or calibrated by means of the signal sequence when the functional unit 1 is inserted, sucked in and filled. For this purpose, the calculation- and evaluation unit 13 can receive the control signals of the central control unit 14, which signalise the operating state of the blood treatment device.

In a particularly preferred embodiment, the safety of the blood treatment is improved by the different operating states of the blood treatment device being compared in the calculation- and evaluation unit 13 with the operating state of the functional unit 1. Thus, a plausibility test can take place. For example, it can be monitored by means of the calculation- and evaluation unit 13 whether the control unit 14 can initiate the blood treatment, which is only supposed to happen when the functional unit 1 is positioned in the attachment unit 7. The control unit 14 only activates the blood treatment device when it has received the corresponding control signal from the calculation- and evaluation unit 13, said control signal signalising that the functional unit has been properly inserted in the attachment unit.

The invention claimed is:

1. A blood treatment device comprising:
    an attachment unit for attaching a functional unit intended for single use for carrying out a blood treatment; and a monitoring unit for monitoring the operability and/or the operating state of the functional unit, wherein the attachment unit comprises a top cover, a bottom contact surface, and an attachment component between the top cover and the bottom contact surface, the attachment unit being configured to house a functional unit such that, when the functional unit is housed in the attachment unit, a bottom surface of the functional unit rests on the bottom contact surface of the attachment unit;

the monitoring unit comprises at least one light transmitter and at least one light receiver that are arranged in or on the top cover and directed downwardly such that light emitted by the at least one light transmitter falls on the top of the functional unit when the functional unit is disposed in the attachment unit, and light reflected from a part of the functional unit or a part of the attachment unit is reflected to the light receiver, and the monitoring unit comprises a calculation and evaluation unit that is configured such that conclusions can be drawn as to a defective state and/or a certain operating state of the functional unit when a functional unit is disposed in the attachment unit, based on the intensity of the light falling on the functional unit and of the light reflected from a part of the functional unit or a part of the attachment unit;

the top cover of the attachment unit is attached to the attachment unit so as to be movable between an open position and a closed position; and the attachment unit comprises a suction unit for creating a vacuum at the bottom contact surface, so that a functional unit can be attached to the bottom contact surface by way of suction power.

2. The blood treatment device according to claim 1, wherein the bottom contact surface of the attachment unit comprises a reflective surface.

3. The blood treatment device according to claim 2, wherein the bottom contact surface comprises a flexible material.

4. The blood treatment device according to claim 1, wherein the top cover of the attachment unit is a pivotable top cover configured as a clamp component, so that a functional unit can be attached in a clamped manner between the bottom contact surface and the pivotable top cover.

5. The blood treatment device according to claim 1, wherein the calculation and evaluation unit of the monitoring unit is configured such that, based on a reduction of intensity of reflected light received by the at least one light receiver, it can be concluded that a functional unit is attached to the attachment unit.

6. The blood treatment device according to claim 1, wherein, when a functional unit is disposed in the attachment unit, the calculation and evaluation unit of the monitoring unit is configured such that, based on a reduction of intensity of reflected light received by the at least one light receiver, it can be concluded that a chamber or a channel of a functional unit is filled with a fluid.

7. The blood treatment device according to claim 6, wherein, when a functional unit is disposed in the attachment unit, the calculation and evaluation unit of the monitoring unit is configured such that a control signal is generated when the calculation and evaluation unit has detected that the chamber and/or the channel of the functional unit is filled with a fluid, and wherein the blood treatment device further comprises a control unit that receives the control signal of the calculation and evaluation unit.

8. The blood treatment device according to claim 6, wherein the calculation and evaluation unit of the monitoring unit is configured such that, when a functional unit is disposed in the attachment unit, based on a reduction of intensity of light received by the at least one light receiver, it can be concluded that the fluid with which the chamber or the channel is filled contains haemoglobin.

9. The blood treatment device according to claim 8, wherein the calculation and evaluation unit of the monitoring unit is configured such that, when a functional unit is disposed in the attachment unit, an alarm signal is generated when the calculation and evaluation unit has detected that the fluid with which the chamber or the channel is filled contains haemoglobin, and wherein the blood treatment device comprises an alarm unit that receives the alarm signal of the calculation and evaluation unit.

10. An arrangement comprising the blood treatment device according to claim 1 and a functional unit intended for single use for carrying out the blood treatment.

11. The arrangement according to claim 10, wherein the functional unit is attached to the attachment unit, the functional unit comprises a housing body that is permeable to light and in which at least one chamber for receiving a fluid and/or at least one channel for carrying a fluid are formed, and the light transmitter and the light receiver are arranged such that light emitted by the light transmitter falls on the chamber and/or the channel of the functional unit.

12. The arrangement according to claim 11, wherein the housing body of the functional unit comprises a housing part formed having trough-shaped recesses, which housing part is sealed by a flat housing part so as to be impermeable to fluids.

13. The arrangement according to claim 12, wherein the flat housing part is a film connected to the housing part formed having trough-shaped recesses.

14. The arrangement according to claim 11, wherein the chamber and/or the channel comprises an opening sealed with a hydrophobic membrane, the at least one light transmitter and the at least one light receiver are arranged such that light emitted by the at least one light transmitter falls on the hydrophobic membrane of the chamber, and light is reflected by the hydrophobic membrane and directed to the at least one light receiver.

15. The arrangement according to claim 14, wherein the calculation and evaluation unit of the monitoring unit is configured such that, based on a reduction of intensity of light received by the at least one light receiver, it can be concluded that the hydrophobic membrane is defective.

16. The blood treatment device of claim 1, further comprising a functional unit disposed in the housing of the attachment unit.

* * * * *